ature Patent [19] [11] 4,250,180
Kane et al. [45] Feb. 10, 1981

[54] METHOD OF TREATING ARRHYTHMIA

[75] Inventors: Vinayak V. Kane, Princeton; Seymour D. Levine, North Brunswick, both of N.J.

[73] Assignee: Ortho Pharmaceutical Corporation, Raritan, N.J.

[21] Appl. No.: 58,057

[22] Filed: Jul. 16, 1979

Related U.S. Application Data

[62] Division of Ser. No. 862,718, Dec. 21, 1977, abandoned.

[51] Int. Cl.³ .................................................. C07D 237/30
[52] U.S. Cl. ..................................... 424/250; 544/237
[58] Field of Search ........................ 544/237; 424/250

[56] References Cited

U.S. PATENT DOCUMENTS 3,225,045  12/1965  Walker ................................ 544/237
3,882,119   5/1975  Nathansohn et al. ............ 260/250 P Primary Examiner—Nicholas S. Rizzo
Attorney, Agent, or Firm—Benjamin F. Lambert

[57] ABSTRACT

Azabicyclic compounds are prepared by reaction of a diene and a diazenediyl compound. The azabicyclic compounds possess cardiovascular activity particularly as antiarrhythmic agents.

4 Claims, No Drawings

METHOD OF TREATING ARRHYTHMIA

This is a division of application Ser. No. 862,718, filed Dec. 21, 1977, and now abandoned.

DESCRIPTION OF THE INVENTION

This invention relates to azabicyclic compounds having the following formula:

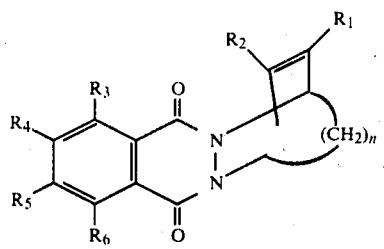

wherein $R_1$ and $R_2$ are selected from hydrogen, loweralkyl, phenyl and —COOR' wherein R' is loweralkyl; $R_3$, $R_4$, $R_5$ and $R_6$ are each selected from hydrogen, loweralkyl, nitro and amino; and n is an integer from 1 to 5, provided that, with the exception of hydrogen, there are not more than two substituents at any one time on the aromatic ring. As used herein the term "loweralkyl" means an alkyl group having 1-5 carbon atoms. The dotted line in the bridgehead indicates the presence of an optional double bond. Those compounds where n is 1 and 4 and $R_1$, $R_2$, $R_3$, $R_4$, $R_5$ and $R_6$ are hydrogen have been reported in the literature [O. L. Chapman and S. J. Dominianni, *J. Org. Chem.*, 31, 3862 (1966); Y. Omote, T. Miyake and N. Sugiyama, *Bull. Chem. Soc. Japan*, 40, 2446 (1967)] but no biological activity has been reported for these compounds. These compounds are not part of the novel compounds of the present invention.

The azabicyclic compounds of the present invention can be prepared by reacting a diene (III) and a phthalazinedione (II) according to the following reaction sequence:

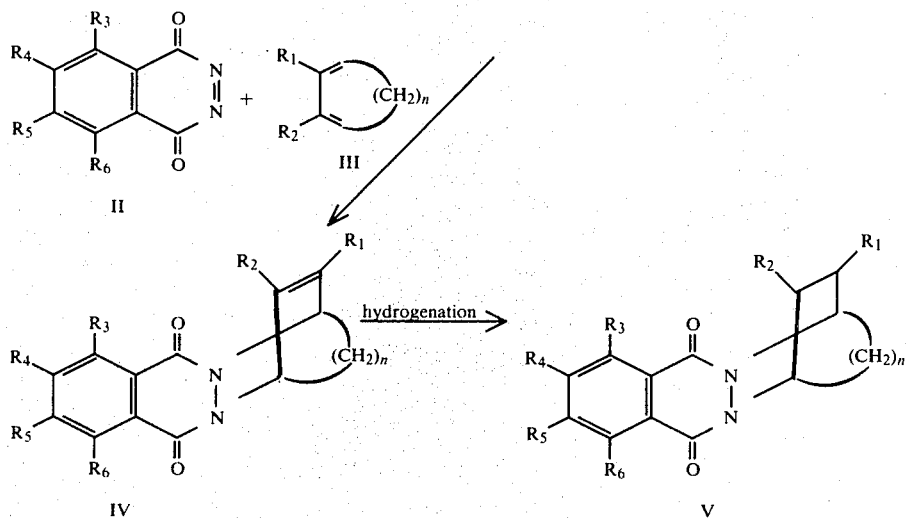

The cycloaddition reaction is preferably carried out in an organic solvent at a temperature between 0° C. and −80° C. It is preferred to carry out the reaction at temperatures between −60° and −30° C. Suitable solvents which may be employed for the cycloaddition reaction include acetone, acetonitrile, dichloromethane and chloroform. The reaction product is collected and purified by techniques known to those skilled in the art. The hydrogenation step is carried out with a suitable hydrogenating agent such as, for example, hydrogen and palladium on charcoal.

The 1,4-phthalazinediones, which are the starting materials for the cycloaddition reaction, are prepared by reacting an alkali metal salt of the appropriately substituted phthalhydrazide with an oxidizing agent such as t-butyl hypochlorite or lead tetraacetate, for example, at a temperature of about −60° C. to −50° C. A method of preparing the starting 1,4-phthalazinediones is described by R. B. Brundrett and E. H. White in *J. Am. Chem. Soc.*, 96, 7497 (1974). The cyclopentadiene starting materials can be made according to N. P. Marullo and J. A. Alford, *J. Org. Chem.*, 33, 2368 (1968). The cyclohexadiene starting materials can be made according to the method of B. Franzus, *J. Am. Chem. Soc.*, 85, 2954 (1963). The cycloheptatriene starting materials can be made according to the method of M. Jones et al, *J. Am. Chem. Soc.*, 91, 7462 (1969) and Berson et al, *J. Org. Chem.*, 33, 1669 (1968). The cyclooctadiene starting materials can be prepared according to the method of A. C. Cope and S. S. Hecht, *J. Am. Chem. Soc.*, 89, 6920 (1967).

The compounds of the present invention possess cardiovascular activity and are particularly active as antiarrhythmic agents. In addition, some of the compounds are effective as postimplantive contragestational agents. An antiarrhythmic agents the compounds are active at dosage levels from about 30 mg. to about 300 mg. The preferred dosage range is from about 50 mg./kg. to about 100 mg./kg.

In practice, the compounds are used in admixture with a pharmaceutically acceptable carrier. Such carriers are prepared according to conventional pharmaceutical compounding techniques and may take a wide variety of forms depending on the form of preparation desired for administration, e.g. oral or parenteral.

In preparing the compositions in oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs, and solutions; or carriers such as starches, sugars, diluents, granulating agents, lubricants, binders, disintegrating agents and the like in the case of oral solid preparations such as, for example, powders, capsules, and tablets. Because of their ease in administration, tablets and capsules represent the most advantageous oral dosage unit form, in which case solid pharmaceutical carriers are employed. If desired, enteric tablets or sugar coated tablets may be prepared by standard techniques. For parenterals, the carrier will usually comprise sterile water, although other ingredients to aid solubility or for preservative purposes, may be included. Injectable suspensions may also be prepared, in which case appropriate liquid carriers, suspending agents and the like may be employed. The pharmaceutical compositions herein will generally contain, per dosage unit, e.g., tablet, capsule, powder, injection, teaspoonful and the like, from about 5 to about 500 mg. of the active ingredient, and preferably, from about 10 to about 250 mg.

The following examples describe the invention in greater particularity and are intended to be a way of illustrating but not limiting the invention.

EXAMPLE 1

1,4-Methano-1,4-dihydropyridazino[1,2-b]phthalazine-6,11-dione

To a solution of t-butyl hypochlorite (3.8 g., 0.038 m.) in acetone (200 ml.), which was cooled to $-60°$, is added the sodium salt of phthalhydrazide (4.8 g., 0.021 g.). After 2.5 hours at $-60°$ to $-50°$, the resulting green reaction mixture is filtered to give a solution of 1,4-phthalazinedione. Cyclopentadiene (2.0 ml.) is added to the cooled green solution ($-50°$) and white crystals precipitate almost immediately. After 10 minutes at $-50°$, the crude product (3.0 g.) is collected by filtration. Recrystallization from $CH_2Cl_2/Et_2O$ affords white microprisms of 1,4-methano-1,4-dihydropyridazino[1,2-b]phthalazine-6,11-dione (1.8 g., 64%), mp 206°–212° C.

When in the above procedure an equivalent amount of an appropriately substituted phthalhydrazide is reacted with an equivalent amount of appropriately substituted cyclopentadiene, the following compounds are obtained:

| $R_1$ | $R_2$ | $R_3$ | $R_4$ | $R_5$ | $R_6$ |
|---|---|---|---|---|---|
| $CH_3$ | $CH_3$ | $NH_2$ | H | H | H |
| H | $CH_3$ | $CH_3$ | H | H | $NH_2$ |
| H | H | H | H | $NH_2$ | $CH_3$ |
| $C_2H_5$ | H | H | $CH_3$ | $NH_2$ | H |
| H | H | H | $n$-$C_3H_7$ | $NH_2$ | H |
| $COOCH_3$ | H | $CH_2OCH_3$ | H | H | $NO_2$ |
| $C_6H_5$ | $C_6H_5$ | H | H | H | H |
| H | $CH_3$ | H | $OCH_3$ | H | H |

EXAMPLE 2

1,4-Methano-1,2,3,4-tetrahydropyridazino[1,2-b]phthalazine-6,11-dione 1,4-Methano-1,4-dihydropyridazino[1,2-b]phthalazine-6,11-dione (1.5 g.) is dissolved in a solution of methylene chloride and methanol (1:1, 60 ml.). After the addition of 10% palladium/charcoal (0.4 g.), the resulting suspension is hydrogenated for one hour under 30 psi. The catalyst is removed by filtration and the filtrate is concentrated to dryness under reduced pressure. The residue is recrystallized from methylene chloride/diethyl ether to afford white granular crystals of 1,4-methano-1,2,3,4-tetrahydropyridazino[1,2-b]phthalazine-6,11-dione (0.5 g., 34%) mp 169°–72° C.

When in the above procedure an equivalent amount of an appropriately substituted 1,4-methano-1,4-dihydropyridazino[1,2-b]phthalazine-6,11-dione is substituted for 1,4-methano-1,4-dihydropyridazino[1,2-b]phthalazine-6,11-dione, the following compounds are obtained:

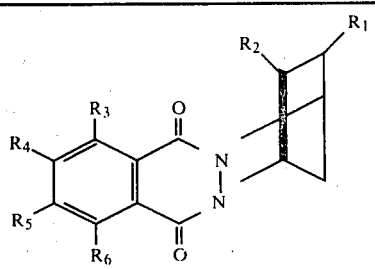

| $R_1$ | $R_2$ | $R_3$ | $R_4$ | $R_5$ | $R_6$ |
|---|---|---|---|---|---|
| $CH_3$ | $CH_3$ | $NH_2$ | H | H | H |
| H | $CH_3$ | $CH_3$ | H | H | $NH_2$ |
| H | H | H | H | $NH_2$ | $CH_3$ |
| $C_2H_5$ | H | H | $CH_3$ | $NH_2$ | H |
| H | H | H | $n$-$C_3H_7$ | $NH_2$ | H |
| $COOCH_3$ | H | $CH_2OCH_3$ | H | H | $NH_2$ |
| $C_6H_5$ | $C_6H_5$ | H | H | H | H |
| H | $CH_3$ | H | $OCH_3$ | H | H |

EXAMPLE 3

1,4-Ethano-1,4-dihydropyridazino[1,2-b]phthalazine-6,11-dione

To a solution of t-butyl hypochlorite (3.8 g., 0.038 m.) in acetone (200 ml.), cooled to $-60°$ is added the sodium salt of phthalhydrazide (4.8 g., 0.021 m.). After 2.5 hours at $-60°$ to $-50°$, the green reaction mixture is filtered to give a solution of 1,4-phthalazinedione. 1,3-Cyclohexadiene (2.0 ml.) is added to the cooled green solution ($-50°$) and white crystals precipitate almost immediately. After 10 minutes at $-50°$, the crude product (3.0 g.) is collected by filtration. Recrystallization from chloroform/acetone affords white microprisms of 1,4-ethano-1,4-dihydropyridazino[1,2-b]phthalazine-6,11-dione, mp $>250°$ C.

When in the above procedure an equivalent amount of an appropriately substituted phthalhydrazide is reacted with an equivalent amount of an appropriately substituted 1,3-cyclohexadiene, the following compounds are obtained:

| R₁ | R₂ | R₃ | R₄ | R₅ | R₆ |
|---|---|---|---|---|---|
| CH₃ | CH₃ | i-C₃H₇ | H | H | NH₂ |
| H | H | H | CH₃ | NH₂ | H |
| CH₃ | H | CH₃ | H | H | OCH₃ |
| COOCH₃ | H | NH₂ | H | H | H |
| H | COOCH₃ | OCH₃ | OCH₃ | H | H |
| H | H | CH₂OCH₃ | H | H | NO₂ |
| H | H | H | H | NH₂ | CH₃ |
| COOCH₃ | COOCH₃ | t-C₄H₉ | H | H | NH₂ |

EXAMPLE 4

1,4-Ethano-1,2,3,4-tetrahydropyridazino[1,2-b]phthalazine-6,11-dione 1,4-Ethano-1,4-dihydropyridazino[1,2-b] phthalazine-6,11-dione is dissolved in a solution of methylene chloride and methanol (1:1, 60 ml.). After the addition of 10% palladium/charcoal (0.4 g.), the resulting suspension is hydrogenated for one hour under 30 psi. The catalyst is removed by filtration and the filtrate is concentrated until crystallization takes place. Filtration gives white microprisms of 1,4-ethano-1,2,3,4-tetrahydropyridazino[1,2-b]phthalazine-6,11-dione (0.9 g., 60%) mp 247°-250° C.

When in the above procedure an equivalent amount of an appropriately substituted 1,4-ethano-1,4-dihydropyridazino[1,2-b]phthalazine-6,11-dione is substituted for 1,4-ethano-1,4-dihydropyridazino[1,2-b]phthalazine-6,11-dione, the following compounds are obtained:

| R₁ | R₂ | R₃ | R₄ | R₅ | R₆ |
|---|---|---|---|---|---|
| CH₃ | CH₃ | i-C₃H₇ | H | H | NH₂ |
| H | H | H | CH₃ | NH₂ | H |
| CH₃ | H | CH₃ | H | H | OCH₃ |
| COOCH₃ | H | NH₂ | H | H | H |
| H | COOCH₃ | OCH₃ | OCH₃ | H | H |
| H | H | CH₂OCH₃ | H | H | NH₂ |
| H | H | H | H | NH₂ | CH₃ |
| COOCH₃ | COOCH₃ | t-C₄H₉ | H | H | NH₂ |

EXAMPLE 5

1,4-Ethano-2,3-methano-1,2,3,4-tetrahydropyridazino[1,2-b]phthalazino-6,11-dione To a solution of t-butyl hypochlorite (12.3 g., 0.12 m.) in acetone (500 ml.), which is cooled to −60°, is added the sodium salt of phthalhydrazide, (12.3 g., 0.067 m.). After 2.5 hours at −60° to −50°, the reaction mixture is filtered to give a solution of 1,4-phthalazinedione. 1,3,5-Cycloheptatriene (12.0 g., 0.13 ml.) is added to the cooled green solution (−50°) and white crystals precipitate almost immediately. After 10 minutes at −50°, the crude product (5.2 g.) is collected by filtration. Recrystallization of ~½ of the crude product (2.5 g.) from chloroform/acetone affords white granular crystals of 1,4-etheno-2,3-methano-1,2,3,4-tetrahydropyridazino[1,2-b]phthalazine-6,11-dione, mp 257°-259° C.

When in the above procedure an equivalent amount of an appropriately substituted phthalhydrazide is reacted with an equivalent amount of an appropriately substituted cycloheptatriene, the following compounds are obtained:

| R₁ | R₂ | R₃ | R₄ | R₅ | R₆ |
|---|---|---|---|---|---|
| H | H | H | CH₃ | H | NH₂ |
| H | H | H | H | NH₂ | H |
| H | C₆H₅ | H | OCH₃ | H | H |
| CH₃ | CH₃ | H | OCH₃ | OCH₃ | H |
| COOCH₃ | H | CH₂OCH₃ | H | H | NH₂ |
| H | CH₃ | H | t-C₄H₉ | H | NH₂ |
| H | H | H | H | NH₂ | CH₃ |
| COOCH₃ | H | H | H | H | NO₂ |

EXAMPLE 6

1,4-Ethano-2,3-methano-1,2,3,4-tetrahydropyridazino[1,2-b]phthalazine-6,11-dione 1,4-Etheno-2,3-methano-1,2,3,4-tetrahydropyridazino[1,2-b]phthalazine-6,11-dione (2.5 g.) is dissolved in a solution of methylene chloride and methanol (1:1, 150 ml.). After the addition of 10% palladium/charcoal (0.6 g.), the resulting suspension is hydrogenated for 1 hour under 30 psi. The catalyst is removed by filtration and the filtrate is concentrated until crystallization takes place. Filtration gives white crystals of crude product (1.7 g., 65%) which are recrystallized from ethyl acetate to afford white microprisms of 1,4-ethano-2,3-methano-1,2,3,4-tetrahydropyridazino[1,2-b]phthalazine-6,11-dione (0.85 g., mp 214°-215° C.).

When in the above procedure an equivalent amount of an appropriately substituted 1,4-etheno-2,3-methano-1,2,3,4-tetrahydropyridazino[1,2-b]phthalazine-6,11-dione is substituted for 1,4-etheno-2,3-methano-1,2,3,4-tetrahydropyridazino[1,2-b]phthalazine-6,11-dione, the following compounds are obtained:

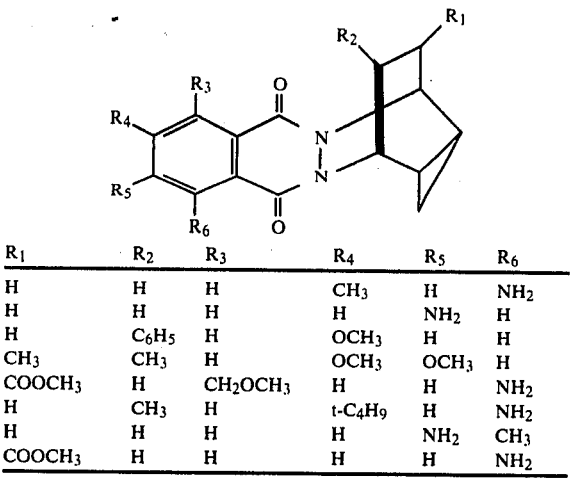

| $R_1$ | $R_2$ | $R_3$ | $R_4$ | $R_5$ | $R_6$ |
|---|---|---|---|---|---|
| H | H | H | $CH_3$ | H | $NH_2$ |
| H | H | H | H | $NH_2$ | H |
| H | $C_6H_5$ | H | $OCH_3$ | H | H |
| $CH_3$ | $CH_3$ | H | $OCH_3$ | $OCH_3$ | H |
| $COOCH_3$ | H | $CH_2OCH_3$ | H | H | $NH_2$ |
| H | $CH_3$ | H | $t\text{-}C_4H_9$ | H | $NH_2$ |
| H | H | H | H | $NH_2$ | $CH_3$ |
| $COOCH_3$ | H | H | H | H | $NH_2$ |

EXAMPLE 7

1,4-Butano-1,4-dihydropyridazino[1,2-b]phthalazine-6,11-dione

To a solution of t-butyl hypochlorite (12.3 g., 0.12 m.) in acetone (500 ml.), which is cooled to −50°, is added to sodium salt of phthalhydrazide (12.4 g., 0.067 m.). The reaction mixture is stirred vigorously for 3 hours at −50° and then filtered to give a solution of 1,4-phthalazinedione. 1,3-Cyclooctadiene (12.0 g., 0.11 m.) is added to the green solution (−50°) and the green solution is warmed to 0°. The solution is kept at 0° until the green color is discharged (1.5 hours). The crude product (5.6 g.) is collected by filtration. Recrystallization of the crude product from methylene chloride-methanol affords white microprisms of 1,4-butano-1,4-dihydropyridazino[1,2-b]phthalazine-6,11-dione (5.0 g., 53%) mp 206°–207° C.

When in the above procedure an equivalent amount of an appropriately substituted phthalhydrazide is reacted with an equivalent amount of an appropriately substituted 1,3-cyclooctadiene, the following compounds are obtained:

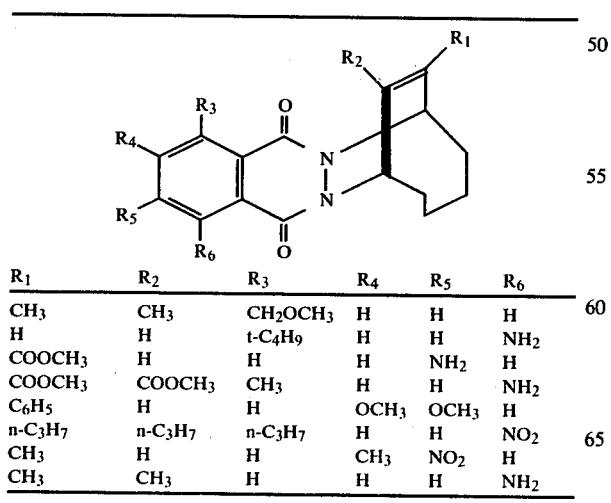

| $R_1$ | $R_2$ | $R_3$ | $R_4$ | $R_5$ | $R_6$ |
|---|---|---|---|---|---|
| $CH_3$ | $CH_3$ | $CH_2OCH_3$ | H | H | H |
| H | H | $t\text{-}C_4H_9$ | H | H | $NH_2$ |
| $COOCH_3$ | H | H | H | $NH_2$ | H |
| $COOCH_3$ | $COOCH_3$ | $CH_3$ | H | H | $NH_2$ |
| $C_6H_5$ | H | H | $OCH_3$ | $OCH_3$ | H |
| $n\text{-}C_3H_7$ | $n\text{-}C_3H_7$ | $n\text{-}C_3H_7$ | H | H | $NO_2$ |
| $CH_3$ | H | H | H | $CH_3$ | $NO_2$ | H |
| $CH_3$ | $CH_3$ | H | H | H | $NH_2$ |

EXAMPLE 8

1,4-Butano-1,2,3,4-tetrahydropyridazino[1,2-b]phthalazine-6,11-dione 1,4-Butano-1,4-dihydropyridazino[1,2-b]phthalazine-6,11-dione (3.0 g.) is dissolved in a solution of methylene chloride and methanol (1:1, 80 ml.). After the addition of 5% palladium/charcoal (1.0 g.), the resulting suspension is hydrogenated for 16 hours under 30 psi. The catalyst is removed by filtration and the filtrate is concentrated to dryness. Recrystallization of the residue from ethyl acetate/hexane affords white granular crystals of 1,4-butano-1,2,3,4-tetrahydropyridazino[1,2-b]phthalazine-6,11-dione (2.2 g., 75%), mp 157°–158° C.

When in the above procedure an equivalent amount of an appropriately substituted 1,4-butano-1,4-dihydropyridazino[1,2-b]phthalazine-6,11-dione is substituted for 1,4-butano-1,4-dihydropyridazino[1,2-b]phthalazine-6,11-dione, the following compounds are obtained:

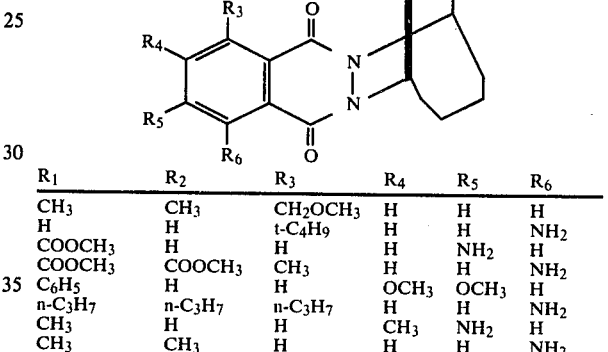

| $R_1$ | $R_2$ | $R_3$ | $R_4$ | $R_5$ | $R_6$ |
|---|---|---|---|---|---|
| $CH_3$ | $CH_3$ | $CH_2OCH_3$ | H | H | H |
| H | H | $t\text{-}C_4H_9$ | H | H | $NH_2$ |
| $COOCH_3$ | H | H | H | $NH_2$ | H |
| $COOCH_3$ | $COOCH_3$ | $CH_3$ | H | H | $NH_2$ |
| $C_6H_5$ | H | H | $OCH_3$ | $OCH_3$ | H |
| $n\text{-}C_3H_7$ | $n\text{-}C_3H_7$ | $n\text{-}C_3H_7$ | H | H | $NH_2$ |
| $CH_3$ | H | H | $CH_3$ | $NH_2$ | H |
| $CH_3$ | $CH_3$ | H | H | H | $NH_2$ |

What is claimed is:
1. A method of treating arrhythmia which comprises administering an effective amount of a compound of the formula:

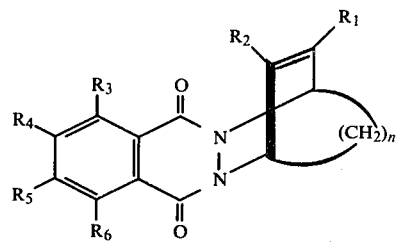

wherein $R_1$ and $R_2$ are hydrogen, loweralkyl, phenyl and COOR' wherein R' is loweralkyl; $R_3$, $R_4$, $R_5$ and $R_6$ are hydrogen, loweralkyl, nitro and amino; and n is an integer from 1 to 5, provided that no more than two substituents are on the aromatic ring at any one time.

2. The method of claim 1 wherein the compound is 1,4-methano-1,4-dihydropyridazino[1,2-b]phthalazine-6,11-dione.

3. The method of claim 1 wherein the compound is 1,4-methano-1,2,3,4-tetrahydropyridazino[1,2-b]phthalazine-6,11-dione.

4. The method of claim 1 wherein the compound is 1,4-ethano-1,4-dihydropyridazino[1,2-b]phthalazine-6,11-dione.

* * * * *